US012342514B1

United States Patent
Wilsey

(10) Patent No.: US 12,342,514 B1
(45) Date of Patent: Jun. 24, 2025

(54) CELLULAR ELECTROMAGNETIC FIELD CONTAINMENT, CHARGING, AND SANITIZING DEVICE

(71) Applicant: Geoffrey Alden Wilsey, Temecula, CA (US)

(72) Inventor: Geoffrey Alden Wilsey, Temecula, CA (US)

( * ) Notice: Subject to any disclaimer, the term of this patent is extended or adjusted under 35 U.S.C. 154(b) by 645 days.

(21) Appl. No.: 17/672,475

(22) Filed: Feb. 15, 2022

Related U.S. Application Data

(60) Provisional application No. 63/150,389, filed on Feb. 17, 2021.

(51) Int. Cl.
| | | |
|---|---|---|
| H05K 9/00 | (2006.01) |
| A61L 2/10 | (2006.01) |
| A61L 2/26 | (2006.01) |
| H02J 7/00 | (2006.01) |
| H02J 50/70 | (2016.01) |

(52) U.S. Cl.
CPC .............. *H05K 9/0007* (2013.01); *A61L 2/10* (2013.01); *A61L 2/26* (2013.01); *H02J 7/0044* (2013.01); *A61L 2202/11* (2013.01); *A61L 2202/122* (2013.01); *H02J 50/70* (2016.02)

(58) Field of Classification Search
CPC ........... H05K 9/0007; A61L 2/10; A61L 2/26; A61L 2202/11; A61L 2202/122; H02J 7/0044; H02J 50/70
See application file for complete search history.

(56) References Cited

U.S. PATENT DOCUMENTS

| | | | |
|---|---|---|---|
| 8,503,182 B2* | 8/2013 | Petrick .................. G06F 1/1633 312/283 |
| 8,723,053 B2* | 5/2014 | Winch ................. H05K 9/0043 174/382 |
| 9,855,351 B2* | 1/2018 | Kim ........................ H04R 1/028 |
| 10,027,150 B2* | 7/2018 | Kvols .................... H02J 50/402 |
| 10,477,741 B1* | 11/2019 | Bae ....................... H04B 1/3883 |
| 11,779,671 B2* | 10/2023 | Yang .......................... A61L 2/26 250/455.11 |
| 2013/0078142 A1* | 3/2013 | Gordon ..................... A61L 2/10 220/660 |
| 2015/0137747 A1* | 5/2015 | Salter ........................ A61L 2/10 320/108 |
| 2016/0042202 A1* | 2/2016 | Murray .................... H04M 1/04 320/108 |
| 2016/0322852 A1* | 11/2016 | Yeh .......................... H04B 5/79 |
| 2016/0372948 A1* | 12/2016 | Kvols .................... H02J 50/402 |
| 2016/0372975 A1* | 12/2016 | Jang ...................... H01F 27/366 |
| 2017/0279294 A1* | 9/2017 | Fujii ..................... H02J 7/0044 |
| 2021/0275700 A1* | 9/2021 | Zhang ...................... A61L 2/24 |
| 2021/0395673 A1* | 12/2021 | Takayama ............. H02J 50/005 |

(Continued)

*Primary Examiner* — Nha T Nguyen
(74) *Attorney, Agent, or Firm* — Plager Schack LLP; Mark H. Plager; Kara K. Verryt

(57) ABSTRACT

A device for electromagnetic field (EMF) containment, charging, and germ cleaning for an electronic device may include a base, a casing extending upward from outer edges of the base, and a cover attached to a top edge of the casing, the cover closing off an interior space defined by engagement of the casing and the base, wherein the casing includes an aluminum based protective film with an aluminum based matrix grid designed to mitigate EMF emissions. The device may also include at least one UV light positioned within the interior space of the device.

9 Claims, 3 Drawing Sheets

(56) References Cited

U.S. PATENT DOCUMENTS

| | | | |
|---|---|---|---|
| 2023/0209787 A1* | 6/2023 | Parry | H05K 9/0094 361/816 |
| 2023/0277700 A1* | 9/2023 | Amir | A61L 2/10 250/455.11 |

* cited by examiner

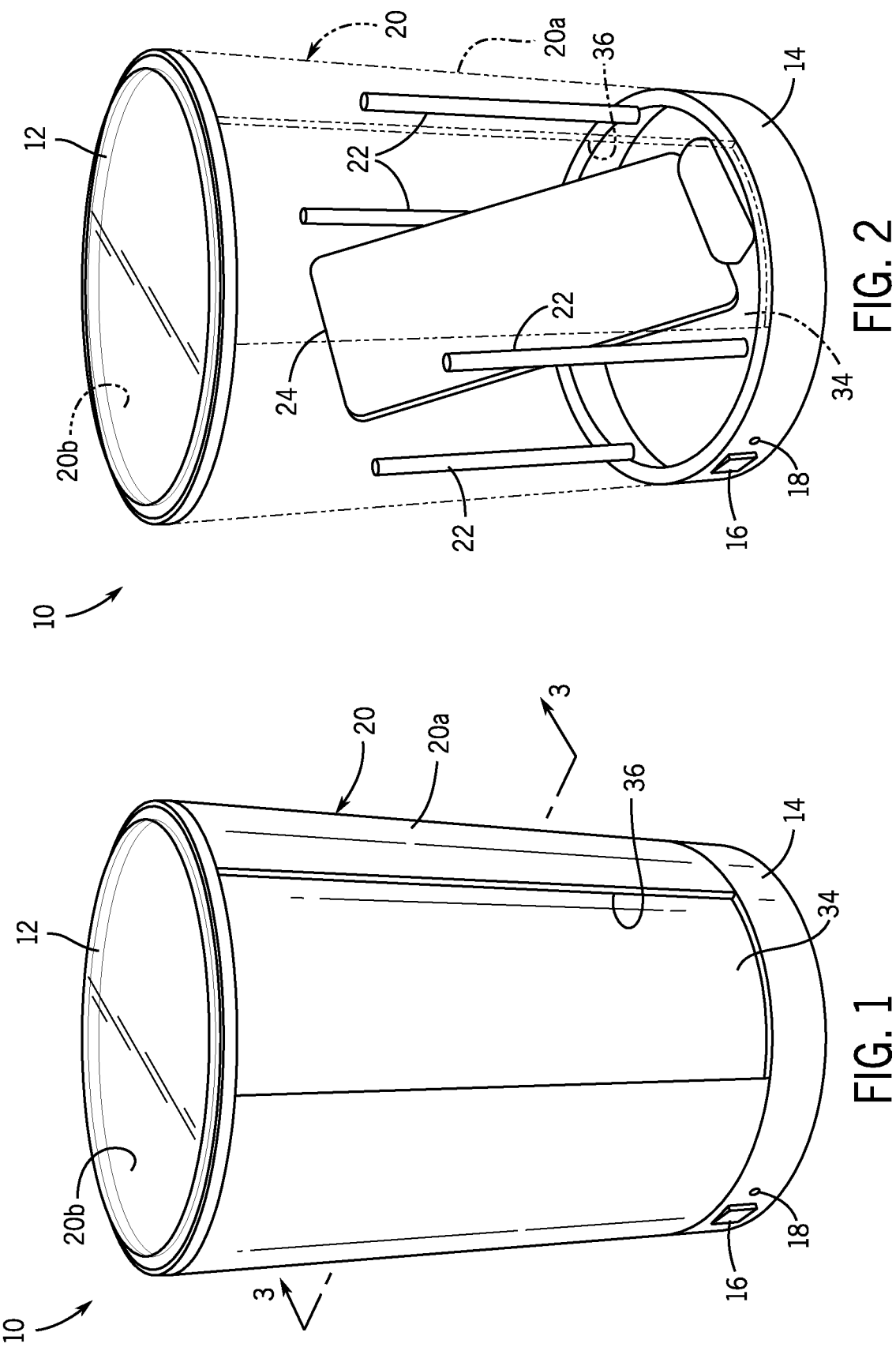

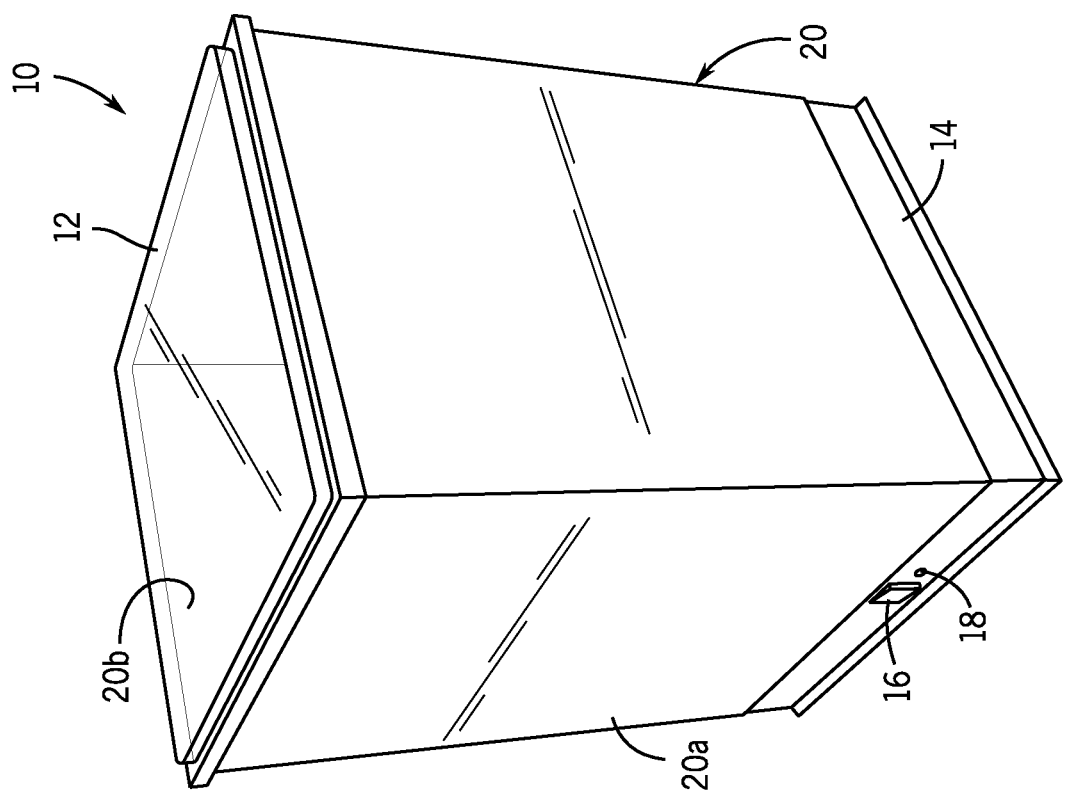
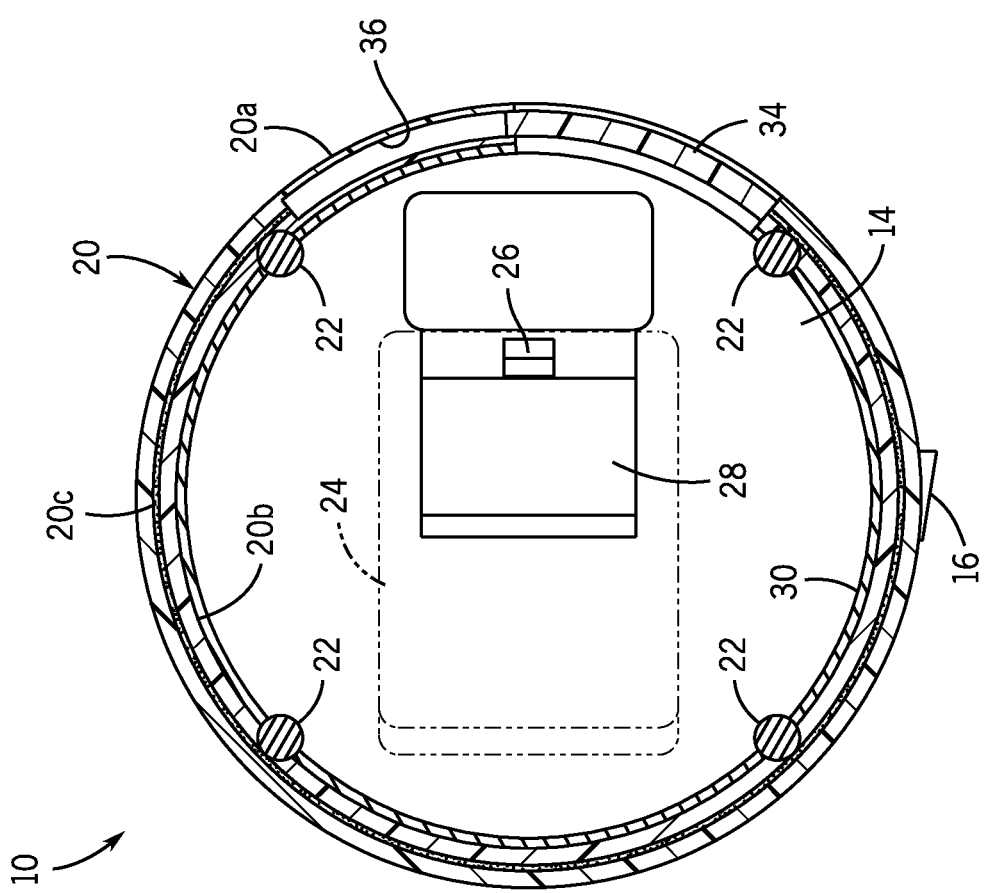

CELLULAR ELECTROMAGNETIC FIELD CONTAINMENT, CHARGING, AND SANITIZING DEVICE

RELATED APPLICATION

This application claims priority to provisional patent application U.S. Ser. No. 63/150,389 filed on Feb. 17, 2021, the entire contents of which is herein incorporated by reference.

BACKGROUND

The embodiments described herein relate generally to accessories for electronic devices and, more particularly, to a device for cellular electromagnetic field (EMF) containment, charging, and sanitizing that limits exposure to EMFs for use with electronic devices, such as smart phones or tablet computers.

As cellular phones become more powerful and, specifically with the advent of 5G, they will continue to emit more harmful levels of EMF that can disrupt sleep and circadian rhythm and cause equilibrium issues, headaches, depression and depressive symptoms, fatigue, dysesthesia, lack of concentration, and changes in memory in people sensitive to EMF. As a secondary problem, cell phones are perfect for transporting bacterial and viral germs that are then placed close to a user's face, introducing the germs into the respiratory system.

Existing devices used to shield or cage EMF for cell phones prevented or negatively impacted vital communication needed to receive critical or emergency transmissions and do not eliminate surface germs that can impact respiratory health while simultaneously providing charging capabilities. Currently, to best protect oneself, it is required that a cell phone be completely powered off or placed in airplane mode while sleeping, which most users are reluctant to do. During the day, powering off the phone or placing it in airplane mode defeats the purpose of having the phone, because communications become unstable or limited.

Therefore, what is needed is a containment device for electronic devices, such as cell phones, wherein the device dramatically reduces the horizontal emitting levels of EMF, creating a safer environment for users while simultaneously allowing for incoming communication, charging, and germ elimination on the surface of the electronic device.

SUMMARY

Some embodiments of the present disclosure include a device for electromagnetic field (EMF) containment, charging, and germ cleaning for an electronic device. The device may include a base, a casing extending upward from outer edges of the base, and a cover attached to a top edge of the casing, the cover closing off an interior space defined by engagement of the casing and the base, wherein the casing includes an aluminum based protective film with an aluminum based matrix grid designed to mitigate EMF emissions. The device may also include at least one UV light positioned within the interior space of the device.

BRIEF DESCRIPTION OF THE FIGURES

The detailed description of some embodiments of the invention is made below with reference to the accompanying figures, wherein like numerals represent corresponding parts of the figures.

FIG. 1 is a perspective view of one embodiment of the present disclosure.

FIG. 2 is a perspective view of one embodiment of the present disclosure.

FIG. 4 is a section view of one embodiment of the present disclosure, taken along line 4-4 in FIG. 3.

FIG. 5 is a perspective view of one embodiment of the present disclosure.

DETAILED DESCRIPTION

Figure 3:
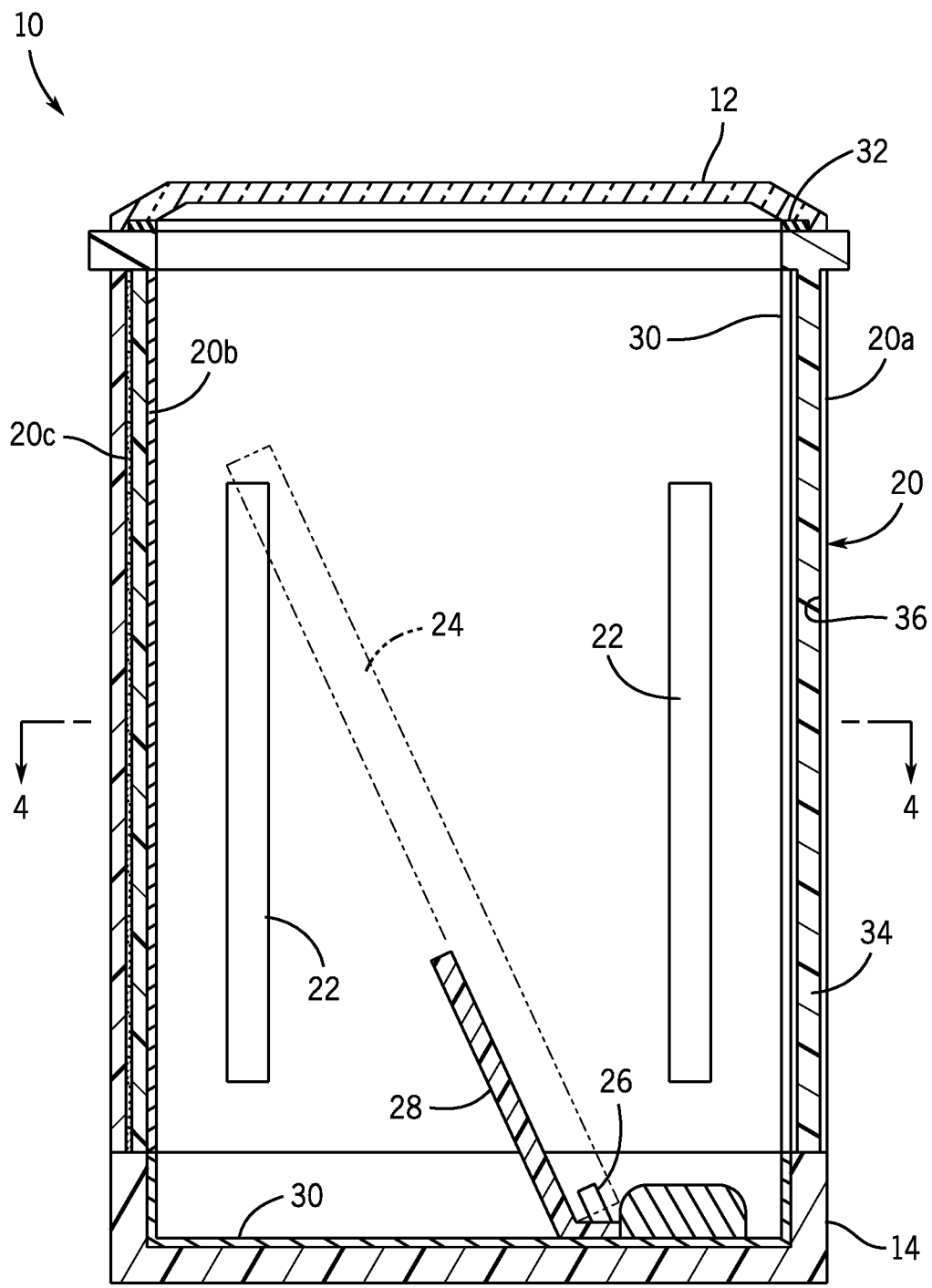
FIG. 3 is a section view of one embodiment of the present disclosure, taken along line 3-3 in FIG. 1.

In the following detailed description of the invention, numerous details, examples, and embodiments of the invention are described. However, it will be clear and apparent to one skilled in the art that the invention is not limited to the embodiments set forth and that the invention can be adapted for any of several applications.

The device of the present disclosure may be used to mitigate electromagnetic field (EMF) exposure and eliminate germs on an electronic device while simultaneously allowing for the use and charging of the electronic device and may comprise the following elements. This list of possible constituent elements is intended to be exemplary only, and it is not intended that this list be used to limit the device of the present application to just these elements. Persons having ordinary skill in the art relevant to the present disclosure may understand there to be equivalent elements that may be substituted within the present disclosure without changing the essential function or operation of the device.

The various elements of the present disclosure may be related in the following exemplary fashion. It is not intended to limit the scope or nature of the relationships between the various elements, and the following examples are presented as illustrative examples only.

By way of example, and referring to FIGS. 1-5, some embodiments of the present disclosure include a device 10 for EMF containment, charging, and sanitizing of an electronic device 24, the device 10 comprising a base 14, a casing 20 extending upward from outer edges of the base 14, and a cover 12 attached to a top edge of the casing 20 distal from the base 14, the cover 12 closing off an interior space defined by the casing 20 and the base 14, wherein the casing 20 comprises an aluminum based matrix grid designed to mitigate electromagnetic field (EMF) emissions. As shown in the Figures, the device 10 further comprises a charging port 26 built into the device 10, such as into the base 12 or into a charging stand 28 extending upward from the base 12 in the interior space of the device 10, wherein the charging port 26 may be compatible with various devices, as desired, such as APPLE products, ANDROID devices, and the like. While not shown in the Figures, a power cord may be operatively attached to the device 10 and may provide power to the charging port 18. In embodiments, at least one ultraviolet (UV) light 22 may be positioned within the interior space of the device 10, wherein the power cord may also be operatively attached to the at least one UV light 22.

In embodiments, the casing 20 may comprise a layered construction. For example, the innermost layer may comprise an inner casing 20*b*, such as an inner plastic tubing or square casing. An internal aluminum based protective film 30 with an aluminum based matrix grid may be applied to an inner surface of the inner casing 20*b*. An outer casing 20*a* may then be attached or applied to the inner casing 20*b*. Thus, the outer casing 20*a* may function as an outermost layer of the casing 20. The outer casing 20a and the inner casing 20b layers may be sealed tougher by, for example, a gel seal layering adhesive 20c.

In embodiments, the base 14 may comprise a modular base with a disconnection option release. A charging stand 28 with a charging port 26, such as a plastic charging stand, may extend upward from the base 14 into the interior space of the device 10. As shown in the Figures, the charging stand 28 may comprise an angled upright wall and a charging stand base, wherein the charging port 26 may extend upwards from the charging stand base. In some embodiments, the charging stand 28 may include insertion guide channels that house an APPLE compatible charging port, an ANDROID compatible charging port, a lightning connector, a USB connector, a micro USB connector, a wireless charging port, and the like.

As described above, at least one UV light 22 may be positioned within the interior space of the device 10. More specifically, the at least one UV light may be attached to an interior surface of the casing 20. For example, and as shown in the Figures, the device 10 may comprise about 4 UV multidirectional vertical germ-killing light strips that may be evenly spaced along an outer edge of the interior space of the device 10. In embodiments, the power cord may be, for example, a 110V power cord with a fuse relay and insulated wiring.

In some embodiments, the device 10 may further comprise a power switch 16 operatively connected to the power cord, the at least one UV light 22, and the charging port 26. The power switch 16 may be used to complete and break an electronic circuit, as desired, to power the device 10 on and off without requiring the power cord to be unplugged from a power source. In yet further embodiments, the device 10 may also comprise a power indicator, such as an LED light 18 designed to illuminate when power is flowing to the electronic components of the device 10. As shown in the Figures, the power switch 16 and the LED light 18 may be positioned on an external surface of the base 14; however, the positioning of the switch 16 and LED light 18 may vary.

As shown in the Figures, a cover 12 may be attached to top edges of the casing 20. In some embodiments, the cover 12 may be sealed to the casing 20 using a top seal 32, such as a rubber sealing strip. In embodiments, the cover 12 may be, for example, a plastic dark coated visibility top using multidirectional metal hinges to provide for top access to the electronic device 24. In other embodiments, the casing 20 may include a sliding door 34 designed to slide into and out of a door pocket 36 built into the casing 20, i.e., between the inner casing 20b and the outer casing 20a.

As shown in the Figures, the device 10 may vary in shape. For example, as shown in FIGS. 1-4, the device 10 may be substantially cylindrical in shape. In another embodiment, such as that shown in FIG. 5, the device 10 may be substantially rectangular cuboid in shape. In fact, the overall shape of the device 10 may vary depending on needs or desires of the user.

The device 10 of the present disclosure may be made of various materials. For example, the outer casing 20a and the inner casing 20b may each comprise a plastic material. Similarly, the base 14 may comprise a plastic material. The cover 12 may also comprise a plastic material that is coated, wherein the plastic may be substantially or partially transparent to allow for visualization of the interior space of the device 10. The device 10 may include multiple aesthetic components, such as decals, applied thereto.

To use the device 10 of the present disclosure, a user may insert the electronic device 24 through the sliding door 34 in the casing 20, through the cover 12, or by lifting the casing 20 from the base 14. Regardless of the method used to insert the electronic device 24 into the containment 20, the electronic device 24 may be positioned on the charging stand 28, and then the device 10 may be closed by either closing the sliding door 34, shutting the cover 12, or replacing the casing 20 onto the base 14. After the electronic device 24 is closed within the device 10, the EMF mitigation may be automatically occurring, even without powering on the device 10. If desired, the user may then engage the switch 16 to start the UV cleaning process, which will destroy bacterial and viral germs on the surfaces of the electronic device 24 while also charging the electronic device 24. When the user receives communications, such as text messages or phone calls, the contact information or other screen display information may be viewed through the cover 12, allowing the user to decide if electronic device 24 is to be removed to respond. In embodiments, the electronic device 24 may be charging anytime it is placed on the charging stand 28. Additionally, any sound from alarms, alerts, calls, safety notices, and the like may be audibly heard and noticeable while in the device 10, allowing the user the option of removing the electronic device 24 to tend to notifications and communications. Thus, use of the device 10 does not impede with use of the electronic device 24, but rather allows the user to leave the electronic device 24 on to receive emergency calls, texts, and messages, while simultaneously mitigating negative EMF exposure.

The above-described embodiments of the invention are presented for purposes of illustration and not of limitation. While these embodiments of the invention have been described with reference to numerous specific details, one of ordinary skill in the art will recognize that the invention can be embodied in other specific forms without departing from the spirit of the invention. Thus, one of ordinary skill in the art would understand that the invention is not to be limited by the foregoing illustrative details, but rather is to be defined by the appended claims.

What is claimed is:

1. A device for electromagnetic field (EMF) containment, charging, and germ cleaning for an electronic device, the device comprising:
   a base;
   a casing extending upward from outer edges of the base; and
   a cover attached to a top edge of the casing, the cover closing off an interior space defined by engagement of the casing and the base,
   wherein:
   the casing comprises an aluminum based protective film with an aluminum based matrix grid designed to mitigate EMF emissions; and
   the base includes a charging stand with a charging port extending upward therefrom, such that the charging stand is positioned within the interior space of the device.

2. The device of claim 1, wherein the base and the casing are removably attached to one another.

3. The device of claim 1, further comprising at least one ultraviolet (UV) light positioned within the interior space of the device.

4. The device of claim 3, wherein the at least one UV light comprises a plurality of UV multidirectional vertical germ-killing light strips that are evenly spaced along an outer edge of the interior space of the device.

5. The device of claim 1, wherein the casing comprises:
an inner casing with the aluminum based protective film applied thereon;
an outer casing positioned along an exterior surface of the inner casing; and
a gel seal layering adhesive sandwiched between the inner casing and the outer casing.

6. The device of claim 1, further comprising a sliding door integrated into the casing.

7. The device of claim 6, wherein:
the casing comprising an inner casing and an outer casing;
a door pocket is defined by a space between the inner casing and the outer casing; and
the door pocket is sized to accommodate the sliding door therein when the sliding door is in an open configuration.

8. The device of claim 1, wherein the cover is transparent.

9. A device for electromagnetic field (EMF) containment, charging, and germ cleaning for an electronic device, the device comprising:

a base;
a casing extending upward from outer edges of the base;
a sliding door integrated into the casing; and
a cover attached to a top edge of the casing, the cover closing off an interior space defined by engagement of the casing and the base,
wherein:
the casing comprises an aluminum based protective film with an aluminum based matrix grid designed to mitigate EMF emissions;
the casing comprises an inner casing and an outer casing;
a door pocket is defined by a space between the inner casing and the outer casing; and
the door pocket is sized to accommodate the sliding door therein when the sliding door is in an open configuration.

\* \* \* \* \*